United States Patent
Gong et al.

(10) Patent No.: US 11,843,021 B2
(45) Date of Patent: Dec. 12, 2023

(54) OPTICAL DETECTION MODULE, METHOD FOR MANUFACTURING OPTICAL DETECTION MODULE, AND OPTICAL DETECTION SUBSTRATE

(71) Applicants: HEFEI BOE OPTOELECTRONICS TECHNOLOGY CO., LTD., Anhui (CN); BOE TECHNOLOGY GROUP CO., LTD., Beijing (CN)

(72) Inventors: Kui Gong, Beijing (CN); Xianxue Duan, Beijing (CN); Zhihai Zhang, Beijing (CN); Tianzhen Liu, Beijing (CN); Haifeng Cui, Beijing (CN); Xuecheng Hou, Beijing (CN)

(73) Assignees: HEFEI BOE OPTOELECTRONICS TECHNOLOGY CO., LTD., Anhui (CN); BOE TECHNOLOGY GROUP CO., LTD., Beijing (CN)

( * ) Notice: Subject to any disclaimer, the term of this patent is extended or adjusted under 35 U.S.C. 154(b) by 376 days.

(21) Appl. No.: 17/425,517

(22) PCT Filed: Jan. 6, 2021

(86) PCT No.: PCT/CN2021/070464
§ 371 (c)(1),
(2) Date: Jul. 23, 2021

(87) PCT Pub. No.: WO2021/139679
PCT Pub. Date: Jul. 15, 2021

(65) Prior Publication Data
US 2022/0093675 A1 Mar. 24, 2022

(30) Foreign Application Priority Data

Jan. 7, 2020 (CN) .......................... 202010014287.9

(51) Int. Cl.
*H01L 27/146* (2006.01)
*A61B 6/00* (2006.01)

(52) U.S. Cl.
CPC ...... *H01L 27/14658* (2013.01); *A61B 6/4208* (2013.01); *H01L 27/14636* (2013.01); *H01L 27/14689* (2013.01)

(58) Field of Classification Search
CPC ............ H01L 27/146; H01L 27/14658; H01L 27/14689; H01L 27/14636;
(Continued)

(56) References Cited

FOREIGN PATENT DOCUMENTS

| CN | 102651322 A | 8/2012 |
|----|-------------|--------|
| CN | 105374748 A | 3/2016 |

(Continued)

OTHER PUBLICATIONS

First Office Action with International Search Report dated Jan. 6, 2022 for application No. CN202010014287.9 with English translation attached.

*Primary Examiner* — Jurie Yun
(74) *Attorney, Agent, or Firm* — Nath, Goldberg & Meyer; Joshua B. Goldberg

(57) ABSTRACT

The present invention provides an optical detection module, a method for manufacturing the same and an optical detection substrate. The optical detection module includes: a base substrate; a switch transistor on a side of the base substrate and including a gate electrode, an active layer, a first electrode and a second electrode; a photosensitive device for sensing light, on a side of the switch transistor away from the base substrate and including a power electrode, a photosensitive layer and an output electrode stacked in sequence, the output electrode being electrically connected to the first electrode of the switch transistor; a barrier on a side of the switch transistor away from the base substrate; and an
(Continued)

insulation portion on the same layer as the output electrode and the barrier and connected between the output electrode and the barrier.

19 Claims, 5 Drawing Sheets

(58) Field of Classification Search
CPC ........... H01L 27/14614; H01L 27/1463; H01L 27/14692; A61B 6/00; A61B 6/4208
See application file for complete search history.

(56) References Cited

FOREIGN PATENT DOCUMENTS

| | | | |
|---|---|---|---|
| CN | 105552086 | A | 5/2016 |
| CN | 107331708 | A | 11/2017 |
| CN | 208422918 | U | 1/2019 |
| CN | 109887936 | A | 6/2019 |
| CN | 109994498 | A | 7/2019 |
| CN | 110047859 | A | 7/2019 |
| CN | 111192889 | A | 5/2020 |
| KR | 100891567 | B1 | 4/2009 |

First Direction

OPTICAL DETECTION MODULE, METHOD FOR MANUFACTURING OPTICAL DETECTION MODULE, AND OPTICAL DETECTION SUBSTRATE

CROSS-REFERENCE TO RELATED APPLICATIONS

This is a National Phase Application filed under 35 U.S.C. 371 as a national stage of PCT/CN2021/070464, filed Jan. 6, 2021, an application claiming the benefit of Chinese Application No. 202010014287.9, filed Jan. 7, 2020, the content of each of which is hereby incorporated by reference in its entirety.

TECHNICAL FIELD

The present invention relates to the field of electronic device, in particular to an optical detection module, a method for manufacturing the same and an optical detection substrate.

BACKGROUND

With the rapid development of the medical device industry, dynamic digital radio (DDR) devices exhibit excellent effects in disease diagnosis. The DDR device mainly includes a dynamic flat panel detector. Compared with a static flat panel detector, the dynamic flat panel detector can also image in real time on the premise of ensuring the image quality, so as to realize quick positioning and fine diagnosis of clinical focuses.

The flat panel detector is provided with photosensitive devices which are arranged in an array and capable of detecting X-rays, and each of the photosensitive devices is connected to a source electrode of one thin film transistor (TFT). The gate electrodes of the thin film transistors corresponding to each row of photosensitive devices are connected to the same control line, and the drain electrodes of the thin film transistors corresponding to each column of photosensitive devices are connected to the same output line, so that the X-ray detection results of the photosensitive devices are output row by row under the control of the control line, and the X-ray intensity of human tissues can be detected in real time.

SUMMARY

As an aspect, an optical detection module is provided. The optical detection module includes: a base substrate; a switch transistor on a side of the base substrate and including a gate electrode, an active layer, a first electrode and a second electrode; a photosensitive device for sensing light, on a side of the switch transistor away from the base substrate and including a power electrode, a photosensitive layer and an output electrode stacked sequentially, the output electrode being electrically connected to the first electrode of the switch transistor; a barrier on a side of the switch transistor away from the base substrate, an orthographic projection of the barrier on the base substrate at least partially overlapping an orthographic projection of the active layer of the switch transistor on the base substrate; and an insulation portion on the same layer as the output electrode and the barrier and connected between the output electrode and the barrier.

In an embodiment, the optical detection module further includes: an insulation layer on a side of the switch transistor away from the base substrate. The output electrode of the photosensitive device is on a side of the insulation layer away from the base substrate. The output electrode of the photosensitive device is electrically connected to the first electrode through a via hole in the insulation layer. The insulation portion extends into the via hole and covers at least a portion of a side wall of the via hole, and the output electrode of the photosensitive device extends into the via hole.

In an embodiment, each of the output electrode and the barrier includes a conductive metal, and the insulation portion includes an insulating metal oxide based on the conductive metal.

In an embodiment, the conductive metal includes aluminum and/or titanium, and the metal oxide includes aluminum oxide and/or titanium oxide.

In an embodiment, the barrier is on a side of the insulation layer away from the base substrate. The entire orthographic projection of the active layer on the base substrate is within the orthographic projection of the barrier on the base substrate.

In an embodiment, the insulation portion has a size less than or equal to 3 μm along a direction from the barrier toward the output electrode.

In an embodiment, the photosensitive layer of the photosensitive device is on a side of the output electrode away from the base substrate, and the power electrode of the photosensitive device is on a side of the photosensitive layer away from the base substrate.

In an embodiment, the active layer of the switch transistor is on a side of the gate electrode of the switch transistor away from the base substrate.

In an embodiment, the photosensitive device is a photodiode.

As an aspect, an optical detection substrate is provided. The optical detection substrate includes a plurality of optical detection modules arranged in rows and columns; a plurality of control lines extending along a row direction; and a plurality of output lines extending along a column direction. The gate electrodes of the switch transistors of the optical detection modules in each row are connected to a same control line, and the second electrodes of the switch transistors of the optical detection modules in each column are connected to a same output line.

As an aspect, a method for manufacturing an optical detection module is provided. The method includes: forming a switch transistor on a side of a base substrate, the switch transistor including a gate electrode, an active layer, a first electrode and a second electrode; forming a barrier, an insulation portion and an output electrode of a photosensitive device for sensing light on a side of the switch transistor away from the base substrate, wherein the barrier, the insulation portion and the output electrode are on a same layer, the insulation portion is connected between the output electrode and the barrier, an orthographic projection of the barrier on the base substrate at least partially overlaps an orthographic projection of the active layer of the switch transistor on the base substrate, and the output electrode is electrically connected to the first electrode of the switch transistor; and forming a photosensitive layer and a power electrode of the photosensitive device on a side of the output electrode away from the base substrate.

In an embodiment, the method includes: forming an insulation layer on a side of the switch transistor away from the base substrate; and forming a via hole in the insulation layer, such that the via hole exposes the first electrode of the switch transistor.

In an embodiment, forming the barrier, the insulation portion and the output electrode of the photosensitive device for sensing light on the side of the switch transistor away from the base substrate, includes: forming a metal material layer in the via hole and on a side of the insulation layer away from the base substrate; forming a protective pattern on a side of the metal material layer away from the base substrate, such that the protective pattern covers portions of the metal material layer in regions corresponding to the barrier and the output electrode, and no protective pattern is on a side wall of the via hole; and performing an oxidation process on the exposed metal material layer on the side wall of the via hole, such that the metal material layer on the side wall of the via hole is oxidized to form the insulation portion.

In an embodiment, forming the protective pattern on the side of the metal material layer away from the base substrate includes: forming a photoresist layer on a side of the metal material layer away from the base substrate; performing exposure and development processes on the photoresist layer to obtain a photoresist pattern; wherein portions of the photoresist pattern in regions corresponding to the barrier and the output electrode have a first thickness, a portion of the photoresist pattern in the via hole has a second thickness smaller than the first thickness, and no photoresist pattern is in a remaining region; patterning the metal material layer in the remaining region in which no photoresist pattern is disposed; and performing an ashing treatment on the photoresist pattern to remove at least one portion of the photoresist pattern on the side wall of the via hole.

In an embodiment, patterning the metal material layer in the region in which no photoresist pattern is disposed includes: removing, by etching, the metal material layer in the region in which no photoresist pattern is disposed.

In an embodiment, patterning the metal material layer in the region in which no photoresist pattern is disposed includes: performing an oxidation process, so that the metal material layer in the remaining region in which no photoresist pattern is disposed is oxidized to an insulating metal oxide material.

In an embodiment, the metal material layer is made of a conductive metal, and the insulation portion is made of an insulating metal oxide based on the conductive metal.

In an embodiment, the conductive metal includes aluminum and/or titanium, and the metal oxide includes aluminum oxide and/or titanium oxide.

In an embodiment, the switch transistor is formed on a side of the base substrate, such that the active layer of the switch transistor is located on a side of the gate electrode of the switch transistor away from the base substrate.

In an embodiment, the barrier, the insulation portion and the output electrode of the photosensitive device for sensing light are formed on the side of the switch transistor away from the base substrate, such that the entire orthographic projection of the active layer on the base substrate is within the orthographic projection of the barrier on the base substrate.

BRIEF DESCRIPTION OF THE DRAWINGS

The accompanying drawings, which are included to provide a further understanding of the present invention and are incorporated in and constitute a part of this specification, illustrate the present invention together with the implementations below, but do not constitute the limitation of the present invention. In the drawings.

DETAILED DESCRIPTION

The followings are detailed description of the specific implementations of the present invention in combination with the drawings. It should be understood that the specific embodiments described herein are only used to illustrate and explain the present invention and are not used to limit the present invention.

Figure 1:
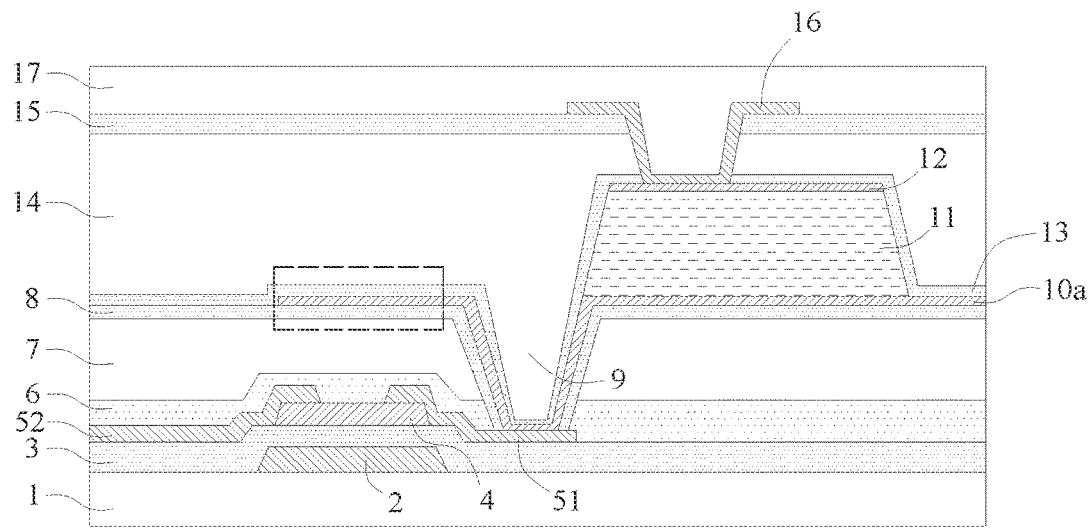
FIG. 1 is a schematic diagram showing a connection between a photodiode and a thin film transistor of a flat panel detector according to the related art.

FIG. 1 is a schematic diagram showing a connection between a photodiode and a thin film transistor of a flat panel detector. An output electrode 10a of a photosensitive device is connected to a first electrode 51 (i.e., a source electrode) of the thin film transistor. As shown in FIG. 1, in the related art, in order to prevent X-rays from adversely affecting the active layer 4 (i.e., the channel) of the thin film transistor, generally an orthogonal projection of a portion (i.e., the portion in a dotted line in FIG. 1) of the output electrode 10a on the base substrate 1 overlaps an orthogonal projection of the active layer 4 of the thin film transistor on the base substrate 1 (i.e., the output electrode 10a is located directly above the active layer of the thin film transistor), thereby blocking X-rays irradiating onto the active layer 4 of the thin film transistor when the flat panel detector operates. However, the flat panel detector adopting the above design generally has the problems such as low detection precision and high failure rate during operation.

After a great deal of experiments and studies are performed on the problems of low detection accuracy and high failure rate of the flat panel detector, the inventors of the present invention have discovered that although a portion (i.e., the portion indicated by the dashed line in FIG. 1) of the orthogonal projection of the output electrode 10a overlapping the orthogonal projection of the active layer 4 (i.e., the channel) of the thin film transistor can prevent X-rays from affecting the active layer 4 as shown in FIG. 1, when the dynamic flat panel detector operates, a potential of the output electrode 10a itself, as an output terminal of the photosensitive device, changes as photo-generated charges in the photosensitive device changes, thereby affecting the transport characteristics of carriers in the channel of the thin film transistor and the I-V characteristics of the thin film transistor.

Figure 2:
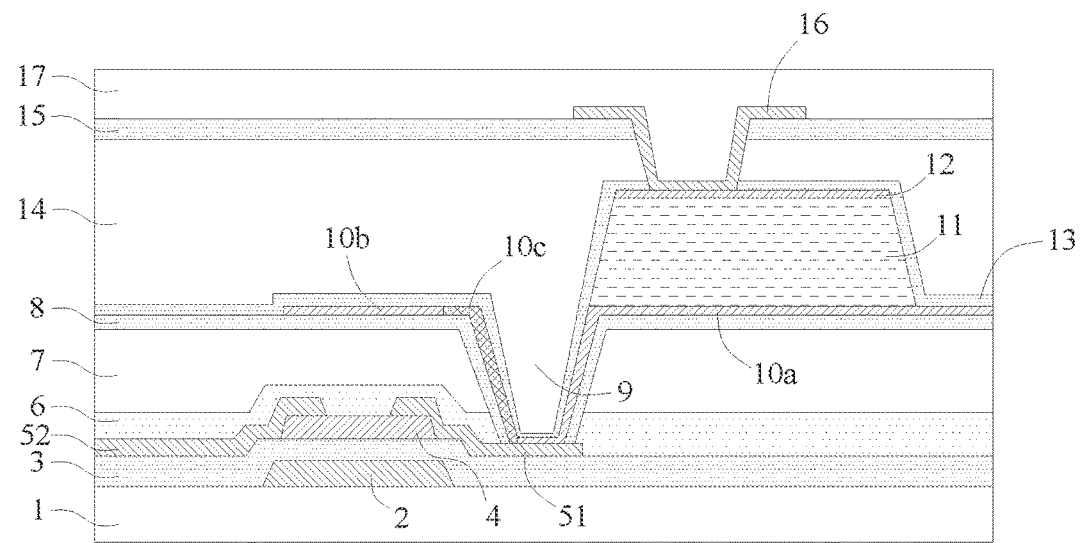
FIG. 2 is a schematic diagram showing an optical detection module according to an embodiment of the present invention.

In order to solve the above problem, an optical detection module is provided. The optical detection module includes a switch transistor and a photosensitive device for sensing light. As shown in FIG. 2, the switch transistor includes a gate electrode 2, an active layer 4, a first electrode 51, and a second electrode 52. The photosensitive device includes a power electrode 12, a photosensitive layer 11, and an output electrode 10a, which are stacked. The output electrode 10a is connected to the first electrode 51. The optical detection module further includes: a barrier (i.e., barrier portion) 10b and an insulation portion 10c.

The barrier 10b is formed on the same layer as the output electrode 10a, an orthographic projection of the barrier 10b on the base substrate 1 overlaps an orthographic projection of the active layer 4 on the base substrate 1, and the barrier 10b is insulated from the active layer 4.

The insulation portion 10c is formed on the same layer as the output electrode 10a and connected between the output electrode 10a and the barrier 10b.

Each of the output electrode 10a and the barrier 10b is made of a conductive metal material, and the insulation portion 10c is made of an insulating metal oxide material obtained by oxidizing the metal material.

In the present invention, the plurality of structures "in the same layer" means that the plurality of structures are formed of the same material layer and are disposed in the same layer in a stacked relationship, but does not mean that the plurality of structures are spaced apart from the base substrate by the same distance or that other layer structures between the plurality of structures and the base substrate are completely the same.

In the optical detection module according to the embodiment of the present invention, the output electrode 10a and the barrier 10b are formed simultaneously, and an orthographic projection of the barrier 10b on the base substrate 1 overlaps an orthographic projection of the active layer 4 on the base substrate 1, so that the X-ray can be blocked from adversely affecting the active layer 4. The metal material between the output electrode 10a and the barrier 10b is oxidized to form an insulating metal oxide material (i.e., the insulation portion 10c), so as to insulate and separate the output electrode 10a from the barrier 10b. When the optical detection module operates, a potential of the barrier 10b does not change, thereby improving the stability and the detection accuracy of the flat panel detector.

In the optical detection module according to the embodiment of the present invention, the metal material between the output electrode 10a and the barrier 10b is oxidized to form a metal oxide, thereby achieving the electrical insulation between the output electrode 10a and the barrier 10b. During the manufacture of the output electrode 10a, the barrier 10b, and the insulation portion 10c, the insulation portion 10c can be obtained by exposing the metal material in a region where the insulation portion 10c is located and oxidizing the metal material in the region with an oxidizing gas. Compared with the scheme of separating the material in the same layer through an etching process in the related art, an insulation interval between the output electrode 10a and the barrier 10b is smaller, such that the barrier 10b has a larger area, thereby improving the blocking effect of the barrier 10b on the X-rays irradiating onto the active layer 4.

It should be noted that, in the related art, when a plurality of electrodes insulated from each other are formed by using a material in a same layer, generally the material in the layer is separated through an etching process. However, generally a minimum line width of an exposed region in the related line exposure process is not less than 3 µm, and in addition, a lateral etch bias when a metal material is etched is generally greater than or equal to 1 µm, that is to say, after two electrodes formed by using the material in the same layer are separated through the etching process, a width of a gap between the two electrodes is at least greater than 4 µm.

However in general, a width of the active layer 4 of the switch transistor in the optical detection module according to the embodiment of the present invention ranges 5 µm to 10 µm. The metal material between the output electrode 10a and the barrier 10b is etched away through an etching process (i.e. the insulation portion 10c does not exist), which will result in an insufficient area of the barrier 10b due to an excessively large gap between the output electrode 10a and the barrier 10b, so that the barrier 10b cannot completely block X-rays irradiating onto the active layer 4 of the switch transistor and cannot prevent X-rays from adversely affecting the active layer 4 of the switch transistor. Therefore, in the embodiment of the present invention, the insulation portion 10c formed by oxidizing the metal material is disposed between the output electrode 10a and the barrier 10b. The above-mentioned problem related to the lateral etching does not exist during the formation of the insulation portion 10c, so that the barrier 10b has a larger area, thereby improving the blocking effect of the barrier 10b on the X-rays irradiating onto the active layer 4, and further improving the stability of the flat panel detector for detecting the X-rays.

A size of the insulation portion 10c is not particularly limited in the present invention. In the present invention, the size of the insulation portion 10c may be determined according to the exposure accuracy limit of the exposure process. For example, in an embodiment, the insulation portion 10c has a size less than or equal to 3 µm along a direction from the barrier 10b to the output electrode 10a. That is, it is directly determined, according to the line width requirement of the exposure process, that the size of the insulation portion 10c in the present invention less than or equal to 3 µm, compared with a situation that the minimum line width of the exposed region in the conventional low-generation line exposure process is generally not less than 3 µm.

In order to improve the protective effect on the active layer 4 of the switch transistor, in an embodiment, the metal material includes aluminum and/or titanium. The metal oxide material includes aluminium oxide and/or titanium oxide. When the metal material includes metal such as aluminum and titanium, accordingly the material of the insulation portion 10c also includes dense ceramic oxide such as aluminum oxide and titanium oxide for blocking the X-rays not perpendicular to the base substrate 1 from irradiating onto the active layer 4, so that both of the barrier 10b and the insulation portion 10c can block the X-rays, thereby improving the protection effect on the active layer 4 of the switch transistor.

In the embodiment of the present invention, other film layers of the optical detection module are not specifically limited. For example, as shown in FIG. 2, the optical detection module further includes: a base substrate 1; at least one insulation layer (e.g., a first insulation layer 6) disposed between the first electrode 51 and the output electrode 10a. The output electrode 10a is disposed on a side of the first electrode 51 away from the base substrate 1 and connected to the first electrode 51 through the via hole 9 in the at least one insulation layer.

Figure 3:
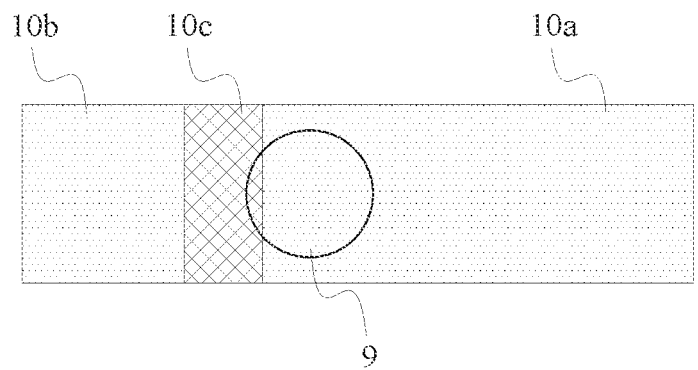
FIG. 3 is a plan view showing a relative positional relationship between a plurality of structures in a film layer in which an output electrode of the optical detection module shown in FIG. 2 is located.

When the metal oxide material includes aluminum oxide and/or titanium oxide, in an embodiment, at least one portion of the insulation portion 10c is in contact with a hole wall of the via hole 9, as shown in FIGS. 2 and 3. In the embodiment of the present invention, when the material of the insulation portion 10c is a ceramic oxide capable of blocking X-rays, at least one portion of the insulation portion 10c extends onto the hole wall of the via hole 9, thereby further increasing an area of a region for blocking the X-ray, and improving the protective effect on the active layer 4 of the switch transistor.

In order to increase the light receiving rate of the photosensitive layer 11, in an embodiment, as shown in FIG. 2, the output electrode 10a is disposed on a side of the photosensitive layer 11 proximity to the base substrate 1.

The structure of the switch transistor is not specifically limited in the embodiments of the present invention. For example, in an embodiment, as shown in FIG. 2, the switch transistor is a bottom-gate type thin film transistor. The barrier 10b and the gate electrode 2 are respectively located on two sides of the active layer 4. Since the barrier 10b can block X-rays irradiating onto the active layer 4, the gate electrode 2 is not necessarily disposed on a side of the active layer 4 distal to the base substrate 1. When the switch transistor is a bottom-gate thin film transistor, a distance between the active layer 4 and the barrier 10b is smaller, thereby further improving the blocking effect of the barrier 10b on the X-rays.

The type of the photosensitive device is not specifically limited in the embodiment of the present invention. For example, the photosensitive device may be a photodiode. The type of the photodiode is not specifically limited in the embodiment of the present invention. The photodiode may be a PIN photodiode, for example. In order to improve the detection accuracy of the optical detection module, in an embodiment, the photosensitive device is a photosensitive device for sensing X-rays.

Other film layers of the optical detection module are not specifically limited in the embodiment of the present invention. For example, as shown in FIG. 2, the optical detection module further includes: a gate insulation layer 3 between the gate 2 and the active layer 4; a first insulation layer 6 on a side of the active layer 4, the first electrode 51 and the second electrode 52 away from the base substrate 1; a first organic film layer 7 on a side of the first insulation layer 6 away from the base substrate 1; a second insulation layer 8 on a side of the first organic film layer 7 away from the base substrate 1; wherein the barrier 10b, the insulation portion 10c and the output electrode 10a are located on a side of the second insulation layer 8 away from the base substrate 1 and are in direct contact with the second insulation layer 8; a metal overlapping layer 16 for providing a potential to the power electrode 12; a third insulation layer 13 and a fourth insulation layer 15 between the metal overlapping layer 16 and the barrier 10b; and a second organic film layer 14 between the third insulation layer 13 and the fourth insulation layer 15.

The metal overlapping layer 16 is connected to the power electrode 12 through a via hole formed in the second organic film layer 14.

In order to avoid the metal overlapping layer 16 from leaking electricity, the optical detection module may further include: a fifth insulation layer 17 formed on a side of the fourth insulation layer 15 and the metal overlapping layer 16 away from the base substrate 1.

An optical detection substrate is provided. The optical detection substrate includes a plurality of optical detection modules as described in the previous embodiments.

In the optical detection substrate according to the embodiment of the present invention, the output electrode 10a and the barrier 10b are formed at the same time during manufacture, and an orthographic projection of the barrier 10b on the base substrate 1 overlaps an orthographic projection of the active layer 4 on the base substrate, thereby preventing the X-rays from adversely affecting the active layer 4. The metal material between the output electrode 10a and the barrier 10b is oxidized to form an insulating metal oxide material, so that the output electrode 10a is insulated and spaced apart from the barrier 10b, therefore a potential of the barrier 10b does not change when the optical detection module operates, thereby improving the stability and accuracy of the dynamic DR device for performing X-ray detection.

During the manufacture of the output electrode 10a, the barrier 10b, and the insulation portion 10c, an insulating metal oxide material (i.e., the insulation portion 10c) is formed by oxidizing a metal material between the output electrode 10a and the barrier 10b, therefore an insulation interval between the output electrode 10a and the barrier 10b is smaller, thereby improving a blocking effect of the barrier 10b against X-rays incident onto the active layer 4.

The circuit structure of the optical detection substrate according to the present invention is not specifically limited. For example, according to an embodiment of the present invention, the optical detection substrate further includes: a plurality of control lines extending along a row direction and a plurality of output lines extending along a column direction.

The plurality of optical detection modules are arranged in rows and columns.

The gate electrodes 2 of the switch transistors in each row of optical detection modules are connected to the same control line.

The second electrodes 52 of the switch transistors in each column of optical detection modules are connected to the same output line.

When the optical detection substrate operates, the control lines corresponding to the plurality of optical detection modules control the switch transistors in rows of the optical detection modules to be turned on sequentially, so that electrical signals generated by the photosensitive devices in each row of the optical detection modules according to the light intensity are output through the plurality of output lines, and thus the real-time detection of the transmission condition of X-rays in human tissues can be realized.

How the optical detection substrate senses the X-ray is not specifically limited in the embodiment of the present invention. For example, the optical detection substrate may cooperate with a fluorescent screen disposed on a receiving surface of the optical detection substrate. When the X-ray irradiates on the fluorescent screen, the fluorescent screen generates light with corresponding intensity, so as to excite the photosensitive device in the optical detection substrate to generate an electrical signal. When the photosensitive device in the optical detection module is a photosensitive device for sensing X-rays, the optical detection substrate can directly perform imaging detection on X-rays.

As shown in FIG. 4 to FIG. 9, a method for manufacturing an optical detection module is further provided. The method is used to manufacture the optical detection module in the previous embodiment. The method includes: forming the barrier 10b, the output electrode 10a, and the insulation portion 10c. For the sake of easy understanding of one of ordinary skill in the art, as shown in FIG. 4 to FIG. 9, a region of the metal material layer 10 corresponding to the output electrode 10a is denoted as a region A, a region of the metal material layer 10 corresponding to the barrier 10b is denoted as a region A, and a region of the metal material layer 10 corresponding to the insulation portion 10c is denoted as a region B, and other regions other than the regions A and B are denoted as regions C. The region B is located between the two regions A.

The method includes: forming a switch transistor on a side of a base substrate, the switch transistor including a gate electrode 2, an active layer 4, a first electrode 51, and a second electrode 52.

A barrier 10b, an insulation portion 10c and an output electrode 10a of a photosensitive device for sensing light are formed on a side of the switch transistor away from the base substrate 1. The barrier 10b, the insulation portion 10c and the output electrode 10a are located on the same layer, and the insulation portion 10c is connected between the output electrode 10a and the barrier 10b. An orthographic projection of the barrier 10b on the base substrate 1 at least partially overlaps (or even completely overlap) an orthographic projection of the active layer 4 of the switch transistor on the base substrate 1, and the output electrode 10a is electrically connected to the first electrode 51 of the switch transistor. A photosensitive layer 11 and a power electrode 12 of the photosensitive device are formed on a side of the output electrode 10a away from the base substrate 1.

In an embodiment, the barrier 10b, the insulation portion 10c, and the output electrode 10a of the photosensitive device for sensing light are formed on a side of the switch transistor away from the base substrate 1, such that an entire orthographic projection of the active layer 4 on the base substrate 1 is within an orthographic projection of the barrier 10b on the base substrate 1.

At least one insulation layer 6, 7 is formed on a side of the switch transistor away from the base substrate 1. A via hole 9 is formed in the at least one insulation layer, such that the via hole 9 exposes the first electrode 51 of the switch transistor.

In the manufacturing method, forming the barrier 10b, the output electrode 10a, and the isolation portion 10c includes steps S10 to S40.

Figure 4:
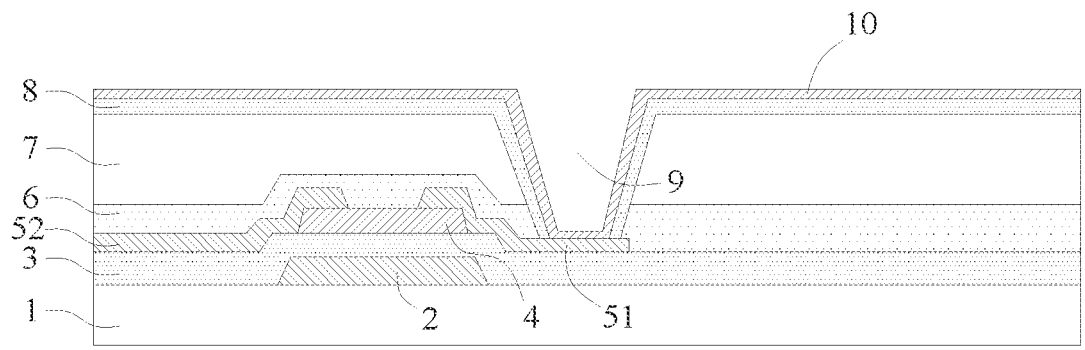
FIGS. 4 to 9 are schematic diagrams showing a method for manufacturing an optical detection module according to an embodiment of the present invention.

At step S10, a metal material layer 10 is formed in the via hole 9 and on a side of the at least one insulation layer away from the base substrate 1 (as shown in FIG. 4).

Figure 7:
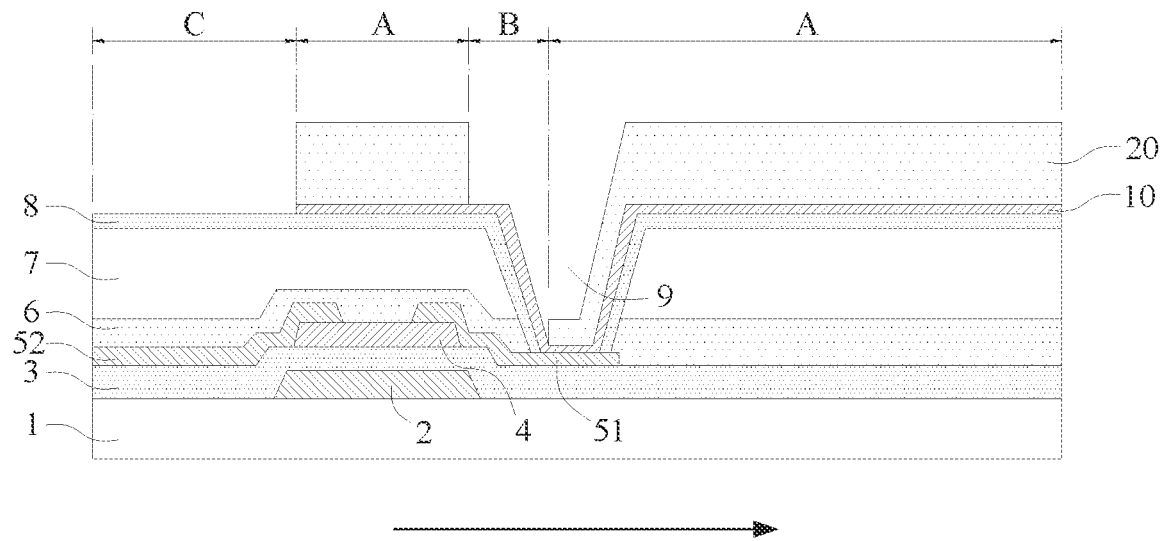

At step S20, a protective pattern 20 is formed on a side of the metal material layer 10 away from the base substrate 1. The protective pattern 20 covers portions of the metal material layer 10 corresponding to the barrier 10b and the output electrode 10a (i.e. the portion in the region A), and the protective pattern 20 is absent on a portion of the metal material layer 10 corresponding to the insulation 10c (i.e. on the portion in the region B or on a side wall of the via hole 9) (as shown in FIG. 7).

Figure 8:
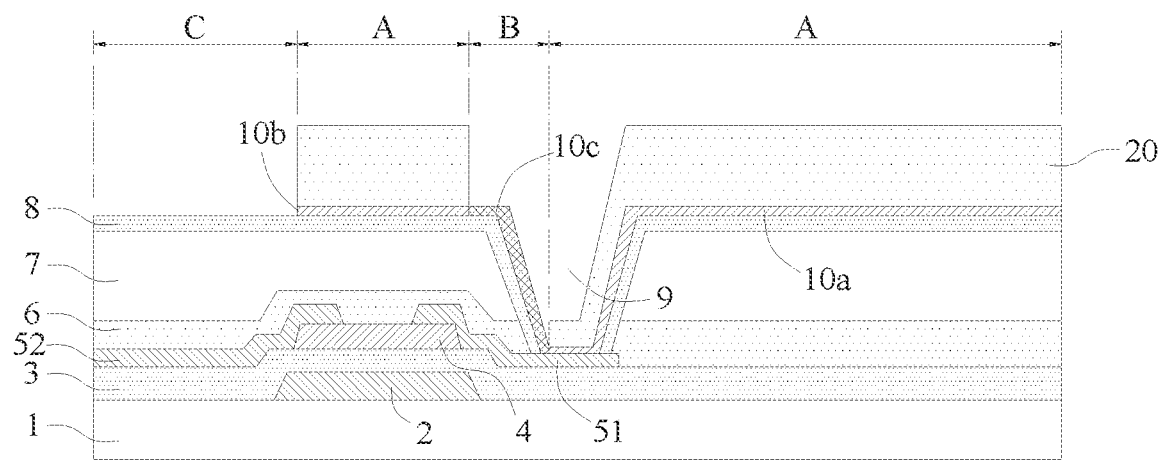

At step S30, the metal material layer on the side wall of the via hole 9 is oxidized by performing an oxidizing process on the metal material layer on the side wall of the via hole, so as to form the barrier 10b, the output electrode 10a, and the isolation portion 10c. The oxidized metal material layer on the side wall of the via hole serves as the insulation portion 10c (as shown in FIG. 8). The portion of the metal material layer 10 above the active layer 4 of the switch transistor serves as the barrier 10b. Both of the metal material layer on a side of the insulation portion 10c away from the barrier 10b along the first direction and the metal material layer on the side wall of the via hole serve as the output electrode 10a of the photosensitive device. The first direction is parallel to the base substrate 1 and points from the second electrode 52 to the first electrode 51 of the switch transistor. In an embodiment, the barrier 10b, the insulation portion 10c, and the output electrode 10a are located in the same layer, and the insulation portion 10c is connected between the output electrode 10a and the barrier 10b. In an embodiment, as shown in the top view of FIG. 3, the barrier 10b and the insulation portion 10c are located on one side (i.e., the left side) of the via hole 9, and the output electrode 10a is located on the side (i.e., the right side) of the via hole 9 opposite to the barrier 10b.

Figure 9:
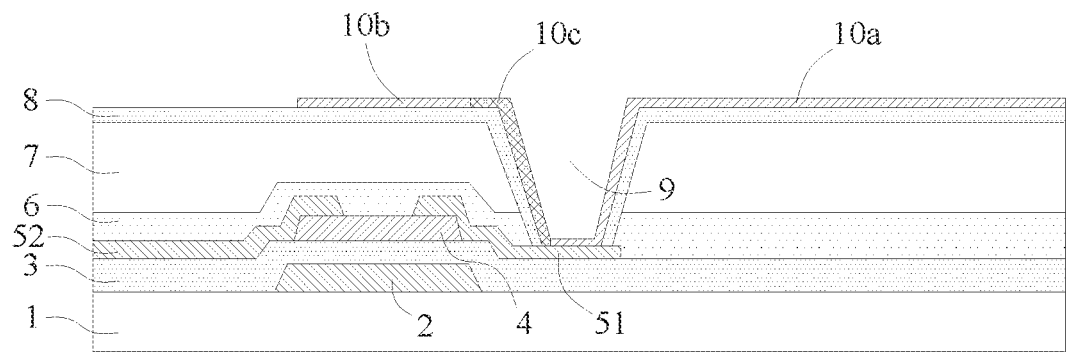

At step S40, the protective pattern 20 remaining on the barrier 10b and the output electrode 10a are removed, as shown in FIG. 9.

In the method for manufacturing an optical detection module according to the embodiment of the present invention, the output electrode 10a and the barrier 10b are formed at the same time, the barrier 10b can prevent X-rays from adversely affecting the active layer 4. In addition, the metal material between the output electrode 10a and the barrier 10b is oxidized to form the insulation portion 10c made of an insulating metal oxide, so as to insulate and separate the output electrode 10a from the barrier 10b. A potential of the barrier 10b does not change when the optical detection module is in an operating state, thereby improving stability and accuracy of the dynamic DR device performing X-ray detection.

In the method for manufacturing the optical detection circuit according to the embodiment of the present invention, the metal material layer 10 in the region B is not covered by the protective pattern 30, and thus, is exposed. The metal material layer 10 in the region B (i.e., on the side wall of the via hole 9) is directly oxidized to form the insulation portion 10c. Compared with the related art in which the material in the same layer is separated through an etching process, the distance between the output electrode 10a and the barrier 10b is smaller, and thus the barrier 10b has a larger area, thereby improving the blocking effect of the barrier 10b on the X-rays irradiating onto the active layer 4.

The metal material layer is made of a conductive metal such as aluminum and/or titanium. The insulation portion is made of a metal oxide such as aluminium oxide and/or titanium oxide.

The method for manufacturing the optical detection circuit according to the embodiment of the present invention further includes: forming the switch transistor on the base substrate 1, the switch transistor including the gate electrode 2, the active layer 4, the first electrode 51 and the second electrode 52, and forming the photosensitive device on the output electrode 10a, the photosensitive device including the photosensitive layer 11, the power electrode 12, a metal overlapping layer 16, etc. Those steps are not specifically limited in the present invention. In an embodiment, the switch transistor is a bottom-gate type switch transistor.

Figure 6:
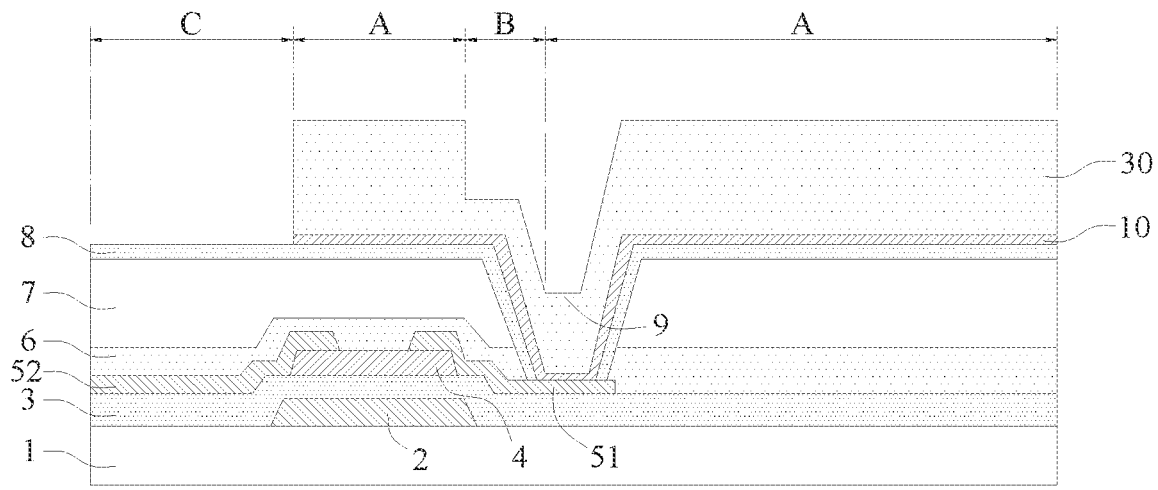

Optionally, between step S10 and step S20, the method further includes: performing a patterning process on the metal material layer 10 to form a patterned metal material layer, as shown in FIG. 6.

The patterning process is not specifically limited in the embodiment of the present invention.

In an embodiment, the metal material in the region (i.e., only in the region C) other than the region covered by the protective pattern may be oxidized into an insulating metal oxide material through an oxidation process, and only the metal material in the region (i.e., the regions A and B) where the barrier 10b, the insulation portion 10C, and the output electrode 10a are located remains, so that a patterned metal material layer is formed.

Figure 10:
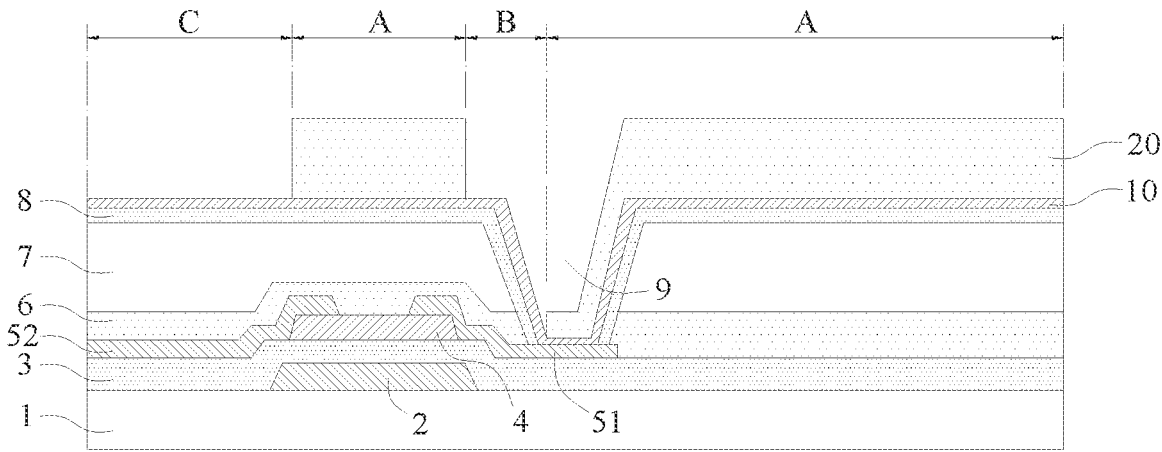
FIGS. 10 to 11 are schematic diagrams showing a method for manufacturing an optical detection module according to an embodiment of the present invention.
Figure 11:
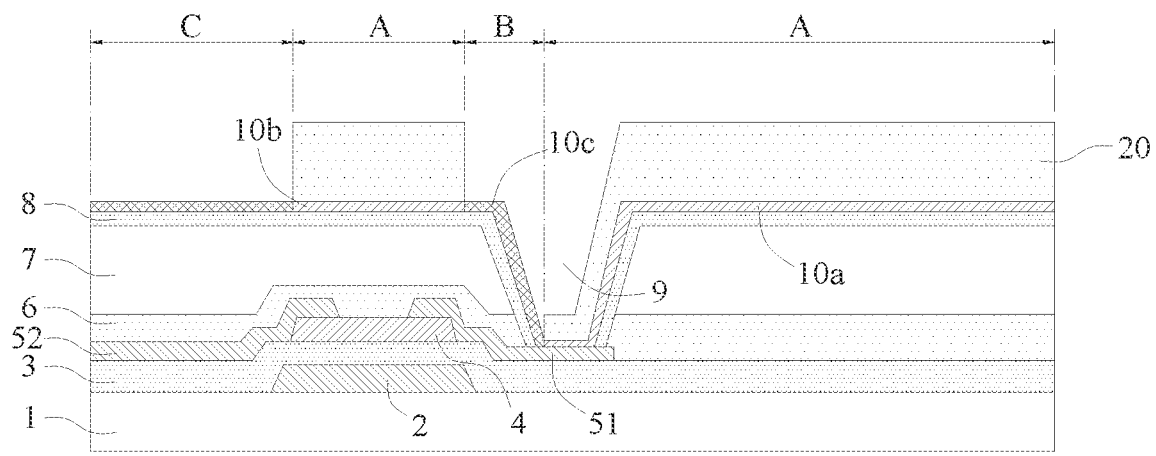

Specifically, when the oxidation process is performed, in order to simplify the process, the step of performing the oxidation process on the metal material in the region (i.e., region C) other than the region covered by the protective pattern and the step of performing the oxidation process on the metal material in the region (i.e., region B) where the insulation portion 10C is located may be performed in the same process. As shown in FIG. 10 to FIG. 11, the protective pattern 20 covers only the region A where the barrier 10*b* is located and the region A where the output electrode 10*a* is located, and the metal material in the region C and the region B is simultaneously oxidized through an oxidation process, thereby forming the output electrode 10*a*, the barrier 10*b*, and the insulation portion 10*c* in one step.

In another embodiment, in order to reduce the material cost of the oxidation process, a photoresist pattern 30 may be coated on the metal material layer 10 in the regions (i.e., two regions A and the region B) corresponding to the output electrode 10*a*, the barrier 10*b* and the insulation portion 10C, and the region (i.e., region C) not covered by the photoresist pattern 30 may be etched, to form a patterned metal material layer, as shown in FIG. 6.

The type of the etching process is not specifically limited in the embodiment of the present invention. For example, the etching process may be a wet etching process.

When the etching process is performed, in an embodiment, as shown in FIG. 4 to FIG. 7, performing a patterning process on the metal material layer 10 to form a patterned metal material layer includes steps S121 and S122.

Figure 5:
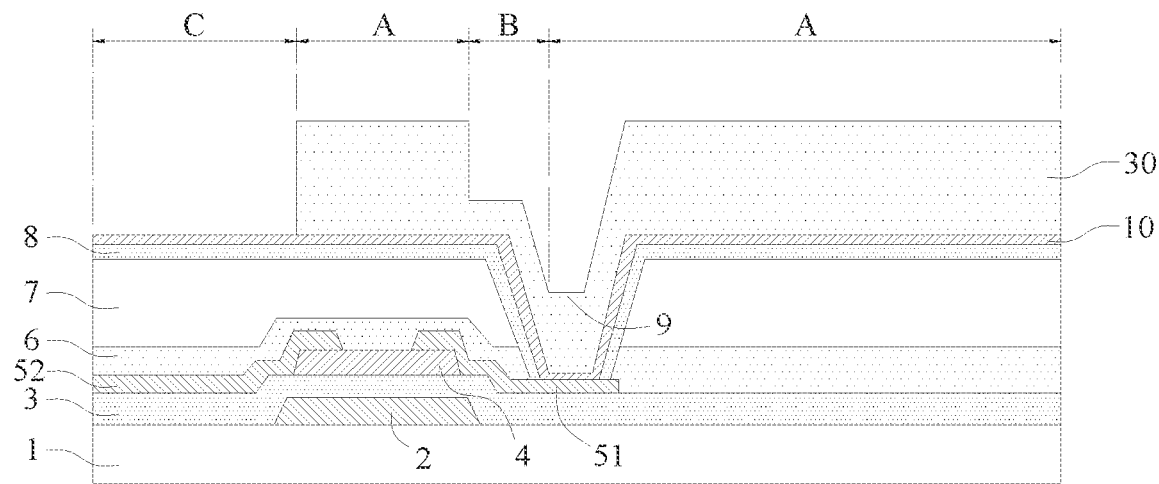

At step S121, a photoresist layer is formed as shown in FIG. 5; step-exposure and development processes are performed on the photoresist layer to obtain a photoresist pattern 30. The photoresist pattern 30 has a first thickness in regions (i.e., two regions A) of the metal material layer 10 corresponding to the barrier 10*b* and the output electrode 10*a*, and has a second thickness less than the first thickness in a region (i.e., region B) of the metal material layer 10 corresponding to the insulation portion 10C, and the photoresist pattern 30 is absent in the other region (i.e., region C).

At step S122, as shown in FIG. 5 to FIG. 6, the metal material layer in the region (i.e., in the region C), where the photoresist pattern 30 is absent, is removed by etching, to form the patterned metal material layer 10.

As shown in FIG. 6 to FIG. 7, the step S20 of forming the protective pattern 20 on a side of the metal material layer 10 away from the base substrate 1 includes: performing an ashing process on the photoresist pattern 30 to remove the photoresist pattern 30 in the regions of the patterned metal material layer 10 corresponding to the insulation portion 10*c*, so that the remaining photoresist pattern 30 in the regions A of the patterned metal material layer 10 corresponding to the barrier 10*b* and the output electrode 10*a* is formed as the protective pattern 20.

In a preferred embodiment, step exposure and development processes are performed on the photoresist layer by using a halftone mask method, so as to obtain photoresist patterns 30 with different thicknesses in various regions. Different processes are performed on the region C and the region B in different steps, that is, the metal material in the region C is etched by using the photoresist pattern 30 to obtain the patterned metal material layer 10, an ashing process is performed on the photoresist pattern 30 to obtain the protective pattern 30, and the metal material in the region B is oxidized by using the protective pattern 30 to obtain the insulation portion 10*c*, thereby reducing the process cost, meanwhile decreasing the size of the insulation portion 10*c* along a direction from the barrier 10*b* to the barrier 10*b*, increasing an area of the barrier 10*b*, and improving the protection effect on the active layer of the switch transistor.

It should be understood that the above implementations are merely exemplary embodiments for the purpose of illustrating the principles of the present disclosure. However, the present disclosure is not limited thereto. It will be apparent to one of ordinary skill in the art that various changes and modifications can be made without departing from the spirit and spirit of the present disclosure, which are also to be regarded as the scope of the present disclosure.

What is claimed is:

1. An optical detection module, comprising:
   a base substrate;
   a switch transistor on a side of the base substrate and comprising a gate electrode, an active layer, a first electrode and a second electrode;
   a photosensitive device for sensing light, on a side of the switch transistor away from the base substrate and comprising a power electrode, a photosensitive layer and an output electrode stacked sequentially, the output electrode being electrically connected to the first electrode of the switch transistor; and
   a barrier on a side of the switch transistor away from the base substrate, an orthographic projection of the barrier on the base substrate at least partially overlapping an orthographic projection of the active layer of the switch transistor on the base substrate; wherein
   the optical detection module further comprises: an insulation portion on the same layer as the output electrode and the barrier and connected between the output electrode and the barrier.

2. The optical detection module of claim 1, further comprising: an insulation layer on a side of the switch transistor away from the base substrate; wherein
   the output electrode of the photosensitive device is on a side of the insulation layer away from the base substrate,
   the output electrode of the photosensitive device is electrically connected to the first electrode through a via hole in the insulation layer,
   the insulation portion extends into the via hole and covers at least a portion of a side wall of the via hole, and
   the output electrode of the photosensitive device extends into the via hole.

3. The optical detection module of claim 2, wherein
   the barrier is on a side of the insulation layer away from the base substrate, and
   the entire orthographic projection of the active layer on the base substrate is within the orthographic projection of the barrier on the base substrate.

4. The optical detection module of claim 1, wherein
   each of the output electrode and the barrier comprises a conductive metal, and
   the insulation portion comprises an insulating metal oxide based on the conductive metal.

5. The optical detection module of claim 4, wherein
   the conductive metal comprises aluminum and/or titanium, and
   the metal oxide comprises aluminum oxide and/or titanium oxide.

6. The optical detection module of claim 1, wherein
   the insulation portion has a size less than or equal to 3 µm along a direction from the barrier toward the output electrode.

7. The optical detection module of claim 1, wherein
   the photosensitive layer of the photosensitive device is on a side of the output electrode away from the base substrate, and
   the power electrode of the photosensitive device is on a side of the photosensitive layer away from the base substrate.

8. The optical detection module of claim 1, wherein the active layer of the switch transistor is on a side of the gate electrode of the switch transistor away from the base substrate.

9. The optical detection module of claim 1, wherein the photosensitive device is a photodiode.

10. An optical detection substrate, comprising:
a plurality of optical detection modules, each of which is the optical detection module of claim 1, arranged in rows and columns;
a plurality of control lines extending along a row direction; and
a plurality of output lines extending along a column direction; wherein
the gate electrodes of the switch transistors of the optical detection modules in each row are connected to a same control line, and
the second electrodes of the switch transistors of the optical detection modules in each column are connected to a same output line.

11. A method for manufacturing an optical detection module, comprising:
forming a switch transistor on a side of a base substrate, the switch transistor comprising a gate electrode, an active layer, a first electrode and a second electrode;
forming a barrier, an insulation portion and an output electrode of a photosensitive device for sensing light on a side of the switch transistor away from the base substrate, wherein the barrier, the insulation portion and the output electrode are on a same layer, the insulation portion is connected between the output electrode and the barrier, an orthographic projection of the barrier on the base substrate at least partially overlaps an orthographic projection of the active layer of the switch transistor on the base substrate, and the output electrode is electrically connected to the first electrode of the switch transistor; and
forming a photosensitive layer and a power electrode of the photosensitive device on a side of the output electrode away from the base substrate.

12. The method of claim 11, further comprising:
forming an insulation layer on a side of the switch transistor away from the base substrate; and
forming a via hole in the insulation layer, such that the via hole exposes the first electrode of the switch transistor.

13. The method of claim 12, wherein
forming the barrier, the insulation portion and the output electrode of the photosensitive device for sensing light on the side of the switch transistor away from the base substrate, comprises:
forming a metal material layer in the via hole and on a side of the insulation layer away from the base substrate;
forming a protective pattern on a side of the metal material layer away from the base substrate, such that the protective pattern covers portions of the metal material layer in regions corresponding to the barrier and the output electrode, and no protective pattern is on a side wall of the via hole; and
performing an oxidation process on the exposed metal material layer on the side wall of the via hole, such that the metal material layer on the side wall of the via hole is oxidized to form the insulation portion.

14. The method of claim 13, wherein forming the protective pattern on the side of the metal material layer away from the base substrate comprises:
forming a photoresist layer on a side of the metal material layer away from the base substrate;
performing step exposure and development processes on the photoresist layer to obtain a photoresist pattern; wherein portions of the photoresist pattern in regions corresponding to the barrier and the output electrode have a first thickness, a portion of the photoresist pattern in the via hole has a second thickness smaller than the first thickness, and no photoresist pattern is in a remaining region;
patterning the metal material layer in the remaining region in which no photoresist pattern is disposed; and
performing an ashing treatment on the photoresist pattern to remove at least one portion of the photoresist pattern on the side wall of the via hole.

15. The method of claim 14, wherein
patterning the metal material layer in the remaining region in which no photoresist pattern is disposed comprises:
removing, by etching, the metal material layer in the remaining region in which no photoresist pattern is disposed.

16. The method of claim 13, wherein
the metal material layer is made of a conductive metal, and
the insulation portion is made of an insulating metal oxide based on the conductive metal.

17. The method of claim 16, wherein
the conductive metal comprises aluminum and/or titanium, and
the metal oxide comprises aluminum oxide and/or titanium oxide.

18. The method of claim 11, wherein
the switch transistor is formed on a side of the base substrate, such that the active layer of the switch transistor is located on a side of the gate electrode of the switch transistor away from the base substrate.

19. The method of claim 11, wherein
the barrier, the insulation portion and the output electrode of the photosensitive device for sensing light are formed on the side of the switch transistor away from the base substrate, such that the entire orthographic projection of the active layer on the base substrate is within the orthographic projection of the barrier on the base substrate.

* * * * *